United States Patent
Paul

(10) Patent No.: US 6,190,036 B1
(45) Date of Patent: Feb. 20, 2001

(54) METHOD AND APPARATUS FOR DETERMINING THE CONCENTRATION OF A LIQUID ICE MIXTURE

(75) Inventor: Joachim Paul, Flensburg (DE)

(73) Assignee: Integral Energietechnik GmbH, Flensburg (DE)

( * ) Notice: Under 35 U.S.C. 154(b), the term of this patent shall be extended for 0 days.

(21) Appl. No.: 09/424,752

(22) PCT Filed: Aug. 27, 1998

(86) PCT No.: PCT/DE98/02522

§ 371 Date: Nov. 29, 1999

§ 102(e) Date: Nov. 29, 1999

(87) PCT Pub. No.: WO99/12023

PCT Pub. Date: Mar. 11, 1999

(30) Foreign Application Priority Data

Aug. 30, 1997 (DE) .............................................. 197 37 983

(51) Int. Cl.$^7$ .................................................. G01N 25/00
(52) U.S. Cl. ............................................... 374/45; 73/61.76
(58) Field of Search ............................ 374/45; 73/61.46, 73/61.76

(56) References Cited

U.S. PATENT DOCUMENTS

| | | | |
|---|---|---|---|
| 3,221,541 | * 12/1965 | Osborne | 73/61.46 |
| 3,552,207 | * 1/1971 | Monk et al. | 73/61.76 |
| 4,226,114 | * 10/1980 | Hagedorn | 73/61.76 |
| 5,980,102 | * 11/1999 | Stulen et al. | 374/45 |

FOREIGN PATENT DOCUMENTS

| | | | |
|---|---|---|---|
| 404066854 | * 3/1992 | (JP) | 73/61.76 |
| 404357446 | * 12/1992 | (JP) | 374/45 |
| 404366731 | * 12/1992 | (JP) | 374/45 |
| WO093024826 | * 12/1993 | (WO) | 374/45 |

* cited by examiner

Primary Examiner—Diego Gutierrez
Assistant Examiner—Lydia M. De Jesús
(74) Attorney, Agent, or Firm—Larson & Larson, PA; James E. Larson

(57) ABSTRACT

Method for determining the ice concentration in a liquid ice mixture (binary ice fluid), with the steps:

separating a partial flow of the fluid and introducing and heating the partial flow into a heat exchange (16) until complete melting takes place, accompanied by the measurement of the inlet temperature $t_A$ and outlet temperature $t_B$, further heating of the fluid flow by an external heat source and return of the partial flow through the heat exchanger (16), accompanied by the measurement of the inlet temperature $t_C$ and outlet temperature $t_O$ of the return partial flow and calculating the ice concentration according to the equation $$X_{ice}=(t_C-t_O-t_B+t_A)\cdot(cp_{fluid}/h_{ice}),$$

in which $cp_{fluid}$ is the specific heat capacity of the binary ice fluid and $h_{ice}$ is the enthalpy of fusion of the binary ice.

6 Claims, 2 Drawing Sheets

METHOD AND APPARATUS FOR DETERMINING THE CONCENTRATION OF A LIQUID ICE MIXTURE

PRIOR APPLICATIONS

This application is a §371 U.S. National Phase application which bases priority on International Application No. PCT/DE98/02522, filed Aug. 27, 1998, which in turn bases priority on German Application No. DE 197 37 983.4, filed Aug. 30, 1997.

BACKGROUND OF THE INVENTION

1. Field of Invention

The invention relates to a method and an apparatus for determining the concentration of a liquid ice mixture.

2. Description of the Prior Art

Liquid ice mixtures comprise suspensions or mixtures of ice crystals or ice fragments in liquid (hereinafter called "binary ice fluid"). Such two-phase fluids are used for cold transport, storage and use. With respect to such fluids it is important to precisely know the ice concentration in order to maintain and/or determine all the process parameters in installations where such liquid ice mixtures are used. It is difficult to precisely determine the ice concentration in a binary ice fluid. The determination of the ice concentration by measuring the electrical conductivity, as known from DE 43 25 793 C2, is not very accurate and cannot be used for any random liquid. Viscosity measurements are difficult to perform even when possible. The pressure drop over a fixed distance is also not a suitable signal, because the viscosity of the liquid is based on the temperature, quantity and quality of additives.

The reason for the use of a binary ice fluid is the latent energy (enthalpy of fusion) of the ice contained in the fluid. This makes it possible to reduce pipeline cross-sections, reduce pumping energy and reduce the size of energy storage devices and heat exchanger surfaces.

The latent energy of binary ice cannot be determined with temperature sensors, because the temperature of the binary ice in the melting range does not or only just changes. Thus, another way for determining the ice concentration is required.

Normally the ice concentration of binary ice is determined by the "calorimetric" method. A volume of binary ice is weighed and its temperature determined. A second volume of sufficiently warm fluid (e.g. water) is weighed and its temperature determined. The two volumes are then mixed and it is then possible by means of the mixture temperature to back-calculate the ice concentration, provided that the mixture no longer contains ice.

However, this method is discontinuous, time-consuming and is only suitable for manual utilization on a laboratory scale.

It is known from DE 43 25 794 C1 to determine the ice concentration in a fluid mixture by measuring the pressure exerted by it.

The problem of the invention is to provide a method and an apparatus for determining the concentration of a liquid mixture, which is applied to a pipeline and which can determine the concentration at least in short intervals.

SUMMARY OF THE INVENTION

The proposed method and the appropriate apparatus for the same make it possible to determine the ice concentration automatically, as well as continuously or discontinuously. It is possible to determine the ice concentration of binary ice in storage devices and pipelines.

Use is made of a method for determining the ice concentration in a binary ice fluid, in which initially part of the flow or storage volume to be measured is removed and introduced into a heat exchanger, accompanied by the simultaneous measurement of the inlet and outlet temperatures and in which by heating the fluid flow and a further return to the heat exchanger, accompanied by a further measurement of the inlet and outlet temperatures of the return flow, the ice concentration is mathematically determined.

DESCRIPTION OF THE DRAWINGS

Further features and advantages of the invention can be gathered from the following description of a preferred embodiment relative to the attached drawings, wherein show.

DETAILED DESCRIPTION OF THE PREFERRED EMBODIMENT

Figure 1:
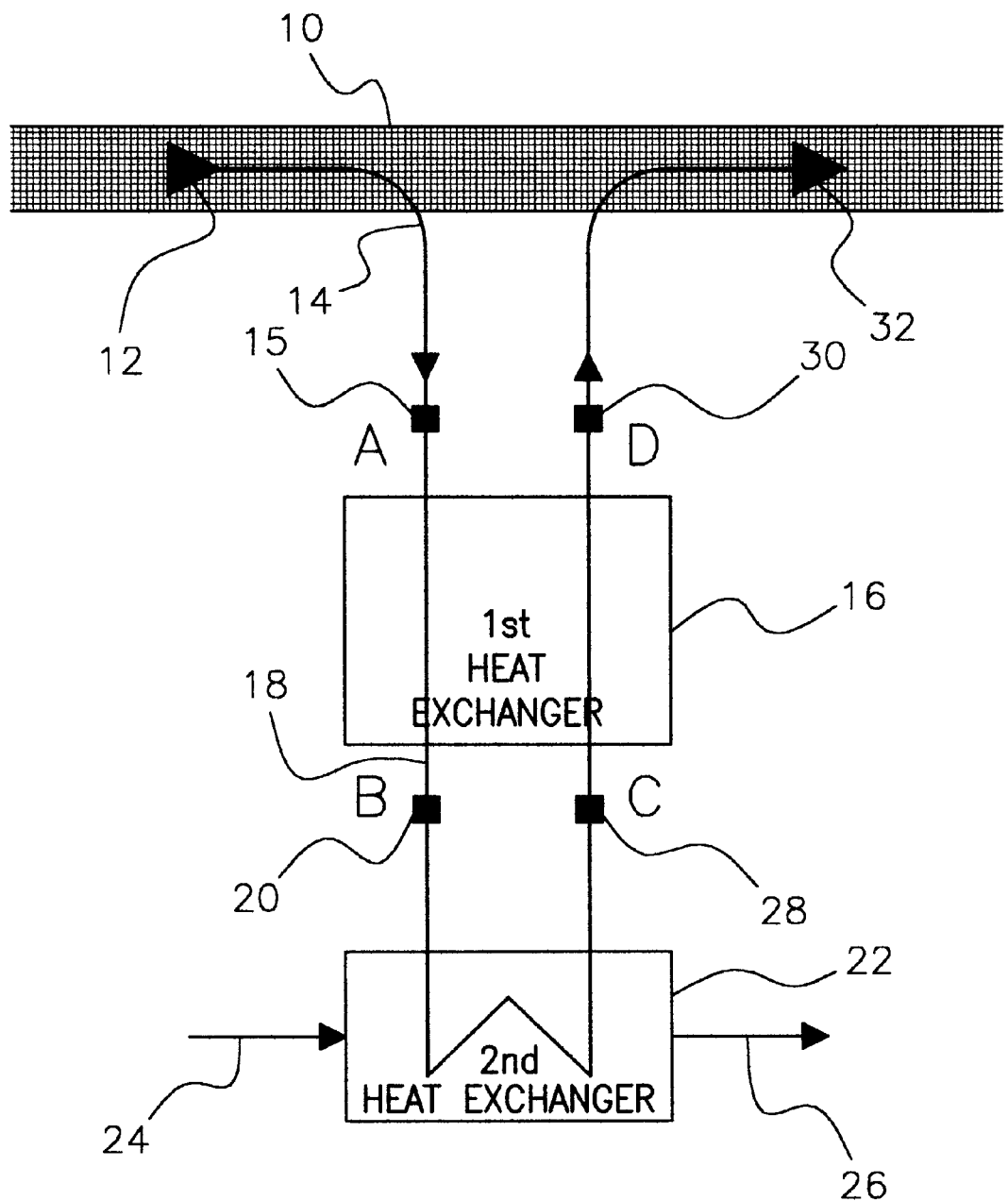
FIG. 1 The diagrammatic construction of an apparatus for ice concentration determination at a pipeline.
Figure 2:
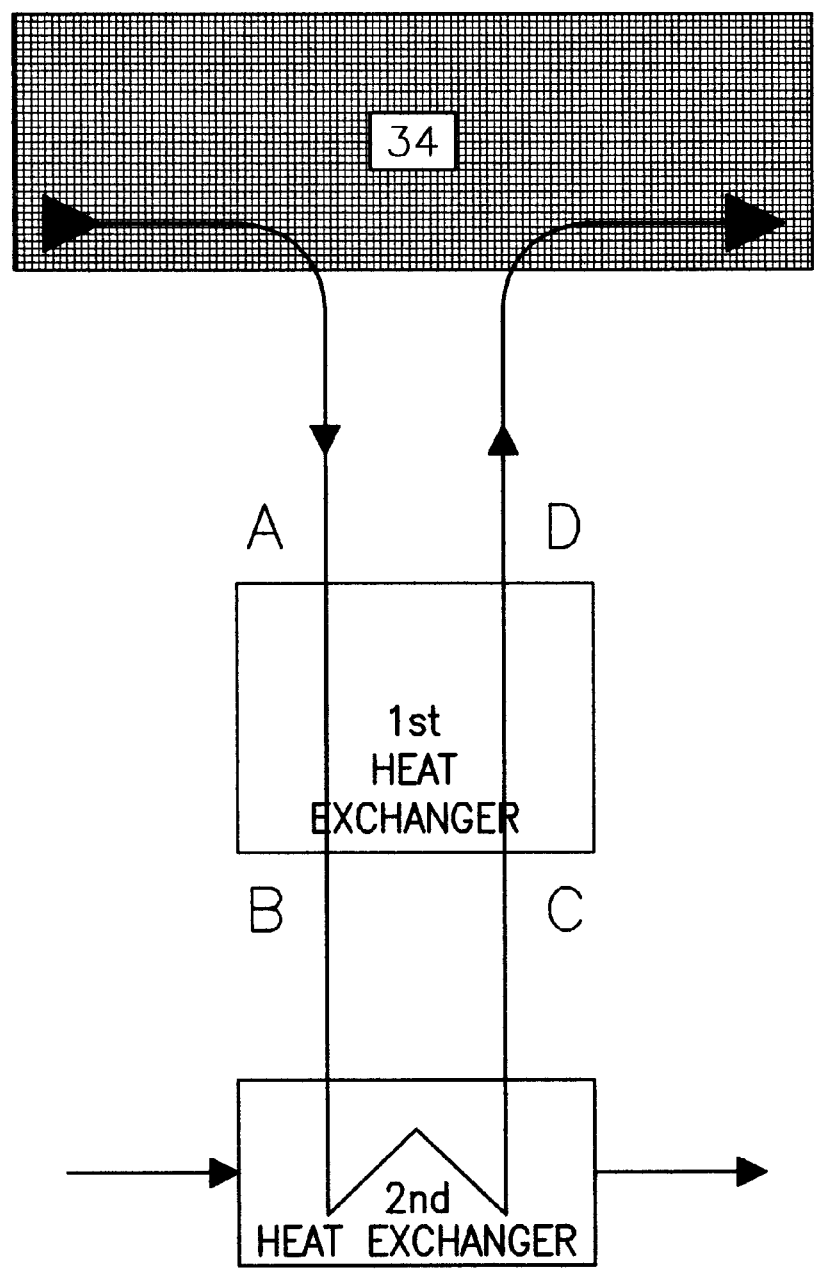
FIG. 2 The arrangement of the apparatus of FIG. 1 at a storage container.

The pipeline 10 shown in FIG. 1 is provided with a device 12 for removing a partial flow feeding the same into a pipeline 14. A temperature sensor 15 at the pipeline 14 measures the binary ice temperature. The binary ice is then melted in a heat exchanger 16, where the heat transferred must be sufficient in order to completely melt the ice. At the outflow line 18 ice-free fluid is present, whose temperature is equal to or higher than the temperature at entry into the heat exchanger 16.

A further temperature sensor 20 is provided on the pipeline on leaving the heat exchanger.

The fluid then enters a second heat exchanger 22, in which it is further heated by an external heat source. As is e.g. shown in FIG. 1, said heat source can be a further water circulation, in which water enters in heated form (reference numeral 24) and leaves again in cooled form (reference numeral 26).

The separated partial flow is then heated from the temperature measured by the temperature sensor 20 to a higher temperature, which is measured by a further temperature sensor 28 prior to reentering the heat exchanger 16. In the heat exchanger the fluid once again loses heat and passes out at a location 30 at a lower temperature. The separated partial flow can now be returned via a device 32 to the main flow and mix with the binary ice.

In the heat exchanger 16 the heated binary ice fluid is cooled and melts or heats the binary ice fluid flowing in the opposite direction, i.e. the enthalpy difference of the binary ice fluid flows between points A and B and C and D are the same, although of different sign.

As the binary ice mass flow in the measuring apparatus remains the same, it is possible to determine the ice concentrations of the binary ice with the aid of four measured temperatures. A volume or mass flow measurement is unnecessary.

The ice concentration is calculated according to the following equation:

$$X_{ice}=(t_C-t_D-t_B+t_A)\cdot(cp_{fluid}/h_{ice}),$$

in which
$X_{ice}$ concentration
$t_C$ Temperature at point C
$t_D$ Temperature at point D
$t_B$ Temperature at point B
$t_A$ Temperature at point A
$cp_{fluid}$ Specific heat capacity of the binary ice fluid
$h_{ice}$ Enthalpy of fusion of the binary ice.

In the case of large pipelines or ice storage devices it is possible to continuously remove a small binary ice mass flow for ice concentration determination, provided that the energy supply resulting from the measurement is relatively small and the energy balance is not permanently disturbed.

With small pipelines or storage devices 34 a discontinuous measurement can be used, if a continuous measurement would excessively disturb the energy balance.

The heat exchanger 22 can be heated both by heated fluid (e.g. water, optionally the cooling water of the refrigerating machine condenser) or also electrically.

Equivalent elements and steps can be substituted for the ones set forth above such that they perform the same function in the same way for achieving the same result.

Having thus described the invention, what is claimed and desired to be secured by Letters Patent is:

1. A method for determining an ice concentration in a main flow of a liquid ice mixture passing through a pipeline, the steps comprising:
   (a) separating a partial flow from the main flow of the liquid ice mixture passing through the pipeline,
   (b) providing a first heat exchanger having first and second inlets and first and second outlets,
   (c) providing first, second, third and fourth temperature sensors at the heat exchanger first inlet, first outlet, second inlet and second outlet respectively,
   (d) introducing the partial flow into the first heat exchanger through the first inlet,
   (e) measuring a temperature $t_A$ at the first sensor,
   (f) heating the partial flow in the first heat exchanger,
   (g) expelling the partial flow out of the first heat exchanger through the first outlet,
   (h) measuring a temperature $t_B$ at the second sensor,
   (i) providing a second heat exchanger having a single inlet and a single outlet,
   (j) introducing the partial flow into the second heat exchanger through the single inlet,
   (k) heating the partial flow in the second heat exchanger,
   (l) expelling the partial flow out of the second heat exchanger through the single outlet,
   (m) measuring a temperature $t_C$ at the third sensor,
   (n) re-introducing the partial flow into the first heat exchanger through the second inlet,
   (o) allowing the partial flow to cool within the first heat exchanger,
   (p) expelling the partial flow out of the first heat exchanger through the second outlet,
   (q) measuring a temperature $t_D$ at the fourth sensor,
   (r) providing a known specific heat capacity $cp_{fluid}$ and a known enthalpy of fusion $h_{ice}$ of the liquid ice mixture, and
   (s) calculating the ice concentration in the liquid ice mixture $X_{ice}$ according to the equation:

$$X_{ice}=(t_C-t_D-t_B+t_A)\,(cp_{fluid}/h_{ice}).$$

2. The method according to claim 1, further comprising the step of re-introducing the partial flow into the main flow of the pipeline after the step of calculating the ice concentration in the liquid ice mixture.

3. The method according to claim 1, wherein the ice of the liquid ice mixture partial flow is melted in the first heat exchanger.

4. The method according to claim 1, wherein the ice of the liquid ice mixture partial flow is melted in the second heat exchanger.

5. A system for determining an ice concentration of a liquid ice mixture flow passing through a main pipeline, the liquid ice mixture having a known specific heat capacity and a known enthalpy of fusion, the system comprising:
   (a) a first heat exchanger having first and second inlets and outlets,
   (b) a second heat exchanger having a single inlet and outlet,
   (c) means for separating a liquid ice mixture partial flow from the main pipeline and directing it through a secondary pipeline, said secondary pipeline interconnecting the first pipeline and the first and second heat exchangers, and
   (d) first, second, third and fourth temperature sensors proximally disposed along the secondary pipeline at the first heat exchanger first inlet and outlet and second inlet and outlet, respectively, each sensor measuring the temperature of the partial flow passing thereby.

6. The system of claim 5, wherein
   (a) the first sensor measures a temperature $t_A$, the second sensor measures a temperature $t_B$, the third sensor measures a temperature $t_C$ and the fourth sensor measures a temperature $t_D$,
   (b) the known specific heat capacity of the liquid ice mixture is $cp_{fluid}$,
   (c) the known enthalpy of fusion of the liquid ice mixture is $h_{ice}$, and
   (d) the ice concentration calculated using the equation:

$$X_{ice}=(t_C-t_D-t_B+t_A)(cp_{fluid}/h_{ice}).$$

* * * * *